US006391344B2

(12) United States Patent
Kosaka et al.

(10) Patent No.: US 6,391,344 B2
(45) Date of Patent: May 21, 2002

(54) METHOD OF PROMOTING SYNTHESIS OF NERVE GROWTH FACTOR

(75) Inventors: Kunio Kosaka; Toshitsugu Miyazaki; Hisatomi Ito, all of Kobe (JP)

(73) Assignee: Nagase & Company, Ltd., Osaka (JP)

( * ) Notice: Subject to any disclaimer, the term of this patent is extended or adjusted under 35 U.S.C. 154(b) by 0 days.

(21) Appl. No.: 09/726,338

(22) Filed: Dec. 1, 2000

(30) Foreign Application Priority Data

Dec. 2, 1999 (JP) ............................................ 11-376276

(51) Int. Cl.$^7$ .............................................. A61K 35/78
(52) U.S. Cl. ........................ 424/725; 424/746; 424/725
(58) Field of Search ................................ 424/725, 745, 424/746

(56) References Cited

U.S. PATENT DOCUMENTS

| | | | | |
|---|---|---|---|---|
| 4,450,097 | A | 5/1984 | Nakatani et al. | ............. 252/404 |
| 5,023,017 | A | 6/1991 | Todd, Jr. | ..................... 252/407 |
| 5,551,258 | A | * 9/1996 | Evans et al. | |
| 5,859,293 | A | * 1/1999 | Bailey et al. | |

FOREIGN PATENT DOCUMENTS

| | | | |
|---|---|---|---|
| JP | 05319187 | A * | 11/1993 |
| JP | 7-25777 | | 1/1995 |
| JP | 7-173059 | | 7/1995 |

OTHER PUBLICATIONS

Haraguchi et al., "Inhibition of lipid peroxidation and superoxide generation by diterpenoids form Romarinus officinalis", Planta Medica, 1995, vol.61, No.4, p. 333–336.*

Luis et al., "Diterpenes from the aeial part of Salvia columbariae", Phytochemistry, 1994, 35(5), p. 1373–1374.*

Neurochem. Int., vol. 30, No. 4/5, P465–474 (1997), Emmett et al., Evaluation of Human Astrocytoma and Glioblastoma Cell Lines for Nerve Growth Factor Release.

J. Neurochemistry, vol. 69, No. 3, P939–946 (1997), Boutros et al., Interferon–β Is a Potent Promoter of Nerve Growth Factor Production by Astrocytes.

Carcinogenesis, vol. 16, No. 9, P2057–2062 (1995) Offord et al., Rosemary components inhibit benzo [a] pyrene–induced genotoxicity in human bronchial cells.

J. Natural Products, vol. 56, No. 8, P1426–1430 (1993) Pariš et al., Inhibitory Effect of Carnosolic Acid on HIV–1 Protease in Cell–Free Assays.

Cancer Res., Feb. No. 54, P701–708 (1994) Huang et al., Inhibition of Skin Tumorigenesis by Rosemary and its Constituents Carnosol and Ursolic Acid.

Food Chem. Toxic, vol. 30, No.6, P483–489 (1992) Smith et al., Protection by Albumin Against the Pro–Oxidant Actions of Phenolic Dietary Components.

Food Chem. Toxic, No. 34, P449–456 (1996) Aruoma et al., An Evaluation of the Antioxidant and Antiviral Action of Extracts of Rosemary and Provencal Herbs.

J. Agric. Food Chem., No. 45, P578–582 (1997), Pearson et al., Inhibition of Endothelial Cell–Mediated Oxdation of Low–Density Lipoprotein by Rosemary and Plant Phenolics.

Cancer Lett., vol. 96, No. 1, P23–29 (1995), Chan et al., Effects of three dietary phytochemicals from tea, rosemary and turmeric on inflammation–induced nitrite production.

Biochem. Pharmacol., vol. 42, No. 9, P1673–1681 (1991) Laughton et al., Inhibition of Mammalian 5–Lipoxygenase and Cyclo–Oxygenase by Flavonoids and Phenolic Dietary Additivies.

Tetrahedron Lett., vol. 32, P4561–4564 (1991), Kawagishi et al, Hericenones D, C and E, stimulators of nerve growth factor (NGF)–synthesis, from the mushroom *Hericium erinaceum* .

Phytochemistry, vol. 32, P175–178 (1993), Kawagishi et al., Chromans, Hericenones F.G and H from the Mushroom *Hericium erinaceum* .

Biochem. Phar., vol. 39, P1813–1816 (1990), Shinoda et al, Stimulation of Nerve Growth Factor Synthesis/Secretion by Propentofylline in Cultured Mouse Astroglial Cells.

Biosci. Biotech. Biochem., vol. 57, P1231–1233 (1993), Yamaguchi et al., Stimulation of Nerve Growth Factor Production by Pyrroloquinoline Quinone and Its Derivatives in Vitro and in Vivo.

Harbone and Baxter, "Phytochemical Dictionary", p. 662, 1993.

Huang et al., "Inhibition of skin, tumorigenesis by rosemary and its constituents carnosol and ursolic acid", Cancer Res., 1; 54(3); 701–8, 1994.

* cited by examiner

Primary Examiner—Leon B. Lankford, Jr.
Assistant Examiner—Ruth Davis
(74) Attorney, Agent, or Firm—Jacobson Holman, PLLC

(57) ABSTRACT

A method of promoting the synthesis of nerve growth factor comprising administering an effective amount of rosemary and/or sage extracts or carnosic acid and/or carnosol as an effective ingredient to a subject requiring such promotion. The present method can safely and efficiently promote the production of NGF in the living body, without being accompanied by a side effect such as a loss of a quantitative balance of hormones in the living body.

7 Claims, No Drawings

METHOD OF PROMOTING SYNTHESIS OF NERVE GROWTH FACTOR

FIELD OF THE INVENTION

The present invention relates to a method of promoting the synthesis of nerve growth factor, more particularly, a method capable of efficiently promoting the synthesis of nerve growth factor in the treatment of nerve-denaturing diseases such as Alzheimer-type dementia and brain ischemia pathologies.

DESCRIPTION OF THE PRIOR ART

Senile dementia has a tendency to increase with the shift to an aging society. This tendency has become an extremely large social problem. A number of diseases are known which are responsible for senile dementia. These are roughly divided into dementia attributable to an organic disorder of the brain, dementia incidental to a disease of other organs than the brain, and dementia attributable to a physical disease due to stress. In particular, the dementia attributable to an organic disorder of the brain, which constitutes the greater part of the causes of dementia, is divided into cerebrovascular dementia and Alzheimer-type dementia due to the differences of the causes.

Currently, it has been known that a drug such as a cerebrovascular dilator exhibits a certain effect on the cerebrovascular dementia. However, the causes of development of Alzheimer-type dementia are not known yet, and a pharmacotherapy and other treatingmethods suitable for preventing the development and progression of the dementia are not known yet. Accordingly, it is greatly desired to develop a drug useful for the treatment of dementia due to an organic disorder of the brain, in particular, Alzheimer-type dementia.

Recently, it has been found that a neurotrophic factor such as nerve growth factor (NGF) secreted from nerve cells has an excellent effect on nerve-denaturing diseases and special attention has been paid to the factor. NGF is a factor necessary and important to the growth and functional maintenance of the nervous tissue. NGF is essential for maturation, differentiation and survival of sensory and sympathetic nerves in the peripheral nervous system as well as for those of large cell cholinergic neurons in the central nervous system. Also, NGF exhibits an effect of preventing denaturing of nerve cells when undergoing a brain lesion. Accordingly, it is believed that an elevation of the NGF level in the living body is effective for treating a disorder of central functions (including Alzheimer-type dementia and cerebrovascular dementia), a lesion of peripheral nerves, a diabetic neuropathy and a disorder of peripheral functions (including amyotrophic lateral sclerosis).

However, NGF is a protein having a high molecular weight of about 13,000 in its monomer form and about 26,000 in its dimer form, and can not pass through the blood-brain barrier. Accordingly, it is necessary to administer NGF intraventricularly, for example, when the treatment of a disorder of central functions is aimed. In addition, it is difficult to prepare NGF in a large amount. Thus, it is very problematic to use NGF per se. Consequently, it is very difficult to use NGF per se clinically.

A method of administering a substance for promoting the synthesis of NGF in the living body, instead of NGF, is also known in the art. For example, Y. Furukawa et al. (FEBS Lett., Vol.208 (1986), p.258 et seq.) discloses that catecholamines (epinephrine, norepinephrine and dopamine) are used as the substance for promoting the synthesis of NGF.

However, they are hormone substances, and therefore, the administration of them causes a problem of losing a quantitative balance of hormones in the living body.

The present invention is addressed to the solution of the above problems. Thus, the object of the present invention is to provide a substance for promoting the synthesis of NGF which allows an effective synthesis of NGF in the living body without being accompanied by a side effect such as a loss of a quantitative balance of hormones in the living body. Another object of the present invention is to provide a method of promoting the synthesis of NGF in the living body.

SUMMARY OF THE INVENTION

The present inventors have intensively searched for a substance having a potent effect of promoting the synthesis of NGF. As a result, they found that rosemary and sage extracts have such an effect. Furthermore, they found that carnosic acid of the formula (I) below and carnosol of the formula (II) below, which are contained in the rosemary and sage extracts, also have the above effect.

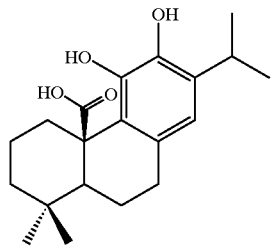

(I)

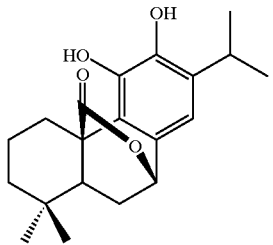

(II)

Thus, the present invention provides a method of promoting the synthesis of nerve growth factor comprising administering an effective amount of at least one plant extract having an effect of promoting the synthesis of nerve growth factor selected from the group consisting of rosemary and sage extracts as an effective ingredient to a subject requiring such promotion.

In a preferred embodiment, the above rosemary and/or sage extracts are those obtained by extracting rosemary and/or sage with ethanol or a mixture of water and ethanol.

Also, the present invention provides a method of producing a plant extract having an effect of promoting the synthesis of nerve growth factor comprising the steps of:

soaking rosemary or sage in ethanol or an aqueous ethanol solution having an ethanol concentration of 80% (v/v) to 100% (v/v) to obtain a first extract;

adding water to the first extract so as to give an ethanol concentration of not greater than 40% (v/v), to deposit a precipitate having an effect of promoting the synthesis of nerve growth factor; and separating the precipitate to obtain the desired plant extract.

Furthermore, the present invention provides a method of promoting the synthesis of nerve growth factor comprising administering an effective amount of at least one ingredient selected from the group consisting of carnosic acid of the above formula (I) and carnosol of the above formula (II) as an effective ingredient to a subject requiring such promotion.

DETAILED DESCRIPTION OF THE INVENTION

In the present invention, the rosemary and/or sage extracts as well as carnosic acid and/or carnosol are generally administered in the form of a preparation for promoting the synthesis of nerve growth factor.

The first preparation according to the present invention contains a rosemary extract or a sage extract. The rosemary and sage extracts used in the present invention are obtained from rosemary (Rosmarinus officinalis L.) and sage (Salvia officinalis L.). Rosemary and sage are plants having a high safety and are widely used for a long time in the West as a herb for medicinal, fragrant and cooking purposes. In the present invention, the rosemary and sage extracts may be used in admixture with each other.

The content of the rosemary and sage extracts contained in the first preparation as an effective ingredient is preferably about 0.0001% to 100% by weight, more preferably about 0.1% to 100% by weight, per 100% by weight of the first preparation. If the content of the extracts is less than 0.0001% by weight, the preparation can not produce an sufficient amount of NGF.

The rosemary or sage extract may be obtained in the following manner, for example. Firstly, the whole plant, leaves and/or petals of rosemary or sage are soaked in an extraction solvent, or refluxed with the extraction solvent. There is no limitation in the type of the extraction solvent used. Examples of the extraction solvent which may be used are organic solvents such as methanol, ethanol, propanol, butanol, propylene glycol, 1,3-butylene glycol, glycerin, acetone, methyl ethyl ketone, ethyl acetate, ethers, chloroform and dichloromethane as well as water. These solvents may be used alone or in combination with one another. In the present invention, it is preferable to use methanol, ethanol, ethyl acetate or a mixture of these solvents with water. More preferably, ethanol or a mixture of water and ethanol is used, in the light of the safety (low toxicity) in the living body.

Preferably, the rosemary and sage extracts are obtained in the following manner, respectively. Firstly, rosemary or sage are soaked in ethanol or an aqueous ethanol solution having an ethanol concentration of 80% (v/v) to 100% (v/v), preferably 90% (v/v) to 100% (v/v) to obtain a first extract.

There is no limitation in the extraction temperature and time to obtain the first extract, and those skilled in the art may determine suitable conditions. Typical conditions include a temperature of about 20° C. to about 50° C. and an extraction time of about 24 hrs to about 72 hors.

Then, water is added to the first extract so as to give an ethanol concentration of not greater than 40% (v/v), preferably not greater than 30% (v/v). By doing so, it is possible to deposit a precipitate having an effect of promoting the synthesis of nerve growth factor from the first extract. Alternatively, the above first extract may be concentrated to one-half to one-twentieth of its original volume, and then, water may be added to the concentrate to deposit the rosemary or sage extract.

There is no limitation in the deposition temperature and time to obtain the rosemary or sage extract from the first extract, and those skilled in the art may determine suitable conditions. Typical conditions include a temperature of about 0° C. to about 25° C. and a deposition time of about 16 hrs to about 48 hors.

By repeating several times the step of adding ethanol or water to the extract so as to give a particular ethanol concentration, the step of dissolving or depositing a precipitate, and the step of filtration, it is possible to obtain the extract described below containing carnosic acid of the formula (I) and carnosol of the formula (II) in a large amount. By using the extract obtained by such extraction procedures, it is possible to remarkably increase the ability to produce NGF.

The first preparation according to the present invention may be made up into suitable forms such as food or drug compositions. Also, the first preparation according to the present invention may be used for both of oral administration and parenteral administration.

In case of making up into food compositions, the above rosemary extract and/or sage extract are mixed with suitable materials which may be commonly used as food materials. Examples of the food materials are rice, wheat, corn, potato, sweet potato, soybean, sea tangle, wakame (Undaria pinnatifida), or agar weed; starch syrup; lactose; glucose; fructose; sucrose; mannitol; and combinations of these materials. In addition, flavoring agents, coloring agents, sweetening agents, edible oils, vitamins and the like may be added to the food compositions. These materials and additives may be used alone or in combination with one another. Also, the food compositions may be made up into a desired shape, if necessary, by adding water.

In case of making up into drug compositions, the above rosemary extract and/or sage extract are mixed with suitable additives. Examples of the additives are surfactants, excipients, coloring agents, preservatives, coating aids and combinations of these additives. These additives may be those commonly used in the production of drug compositions and are not limited to particular ones. More specific examples of the additives are lactose, dextrin, sucrose, mannitol, corn starch, sorbitol, crystalline cellulose, polyvinylpyrrolidone and combinations of these additives. Also, flavoring agents, sweetening agents and the like maybe added to the drug compositions. In addition, other drugs may be added to the drug compositions, if necessary.

There is no limitation in dosage forms of the drug compositions and they may be produced in suitable dosage forms according to a conventional process. For oral administration, in particular, the compositions may be prepared in the forms of capsules, tablets, powder, slow-releasing agents and the like. For parenteral administration, the compositions may be prepared in the forms of injections, infusions and the like.

There is no limitation in the content of the above suitable materials and additives and the compositions may be produced depending on the content of the above rosemary extract and/or sage extract.

The second preparation according to the present invention contains carnosic acid of the above formula (I) or carnosol of the above formula (II). In the present invention, carnosic acid of the formula (I) and carnosol of the formula (II) may be used in admixture with each other.

The content of carnosic acid of the formula (I) and carnosol of the formula (II) contained in the second preparation as an effective ingredient is preferably about 0.00001% to 100% by weight, more preferably about 0.001% to 100% by weight, per 100% by weight of the second preparation. If the content of the above ingredients is less than 0.00001% by weight, the preparation can not promote the production of NGF sufficiently.

Although carnosic acid of the above formula (I) and carnosol of the above formula (II) may be prepared by chemical synthesis, in general, they may be prepared by isolation from a plant extract, preferably from the above rosemary or sage extract. Typically, carnosic acid of the formula (I) and carnosol of the formula (II) are prepared by removing impurities from the above rosemary or sage extract through various column chromatographic means. Those skilled in the art can easily identify by well known means such as $^1$H-NMR or $^{13}$C-NMR that the substance thus obtained is carnosic acid of the formula (I) or carnosol of the formula (II).

Similar to the above first preparation, the second preparation according to the present invention may also be made up into suitable forms such as food or drug compositions, and may be used for both of oral administration and parenteral administration.

EXAMPLES

The present invention is illustrated in more detail by the following examples, but it is not limited thereto.

Example 1

Rosemary (whole plant, 60 g) was soaked in aqueous 90% ethanol solution (300 ml), and extracted at 40° C. for 48 hrs. The resultant solution was concentrated to a volume of 100 ml. After the concentration, the concentrate was filtered to remove insoluble materials. Purified water (200 ml) was added to the filtrate and the mixture was allowed to stand overnight at 4° C. Subsequently, the mixture was again filtered to obtain a rosemary extract (dry weight 3.5 g) which is insoluble part.

Human glioblastoma cells (T98G, Cell line) were seeded in a MEM medium containing fetal bovine serum (10%; Gibco), sodium pyruvate (×1; Gibco) and nonessential amino acids (×1; Gibco) in wells of a flat-bottom 96-well plate (Corning), in a cell density of $2 \times 10^4$/well, and cultivated in a $CO_2$ incubator (37° C., 5% $CO_2$) for 3 days. The medium was then replaced by an Opti-MEM medium (containing 5 mg/ml of bovine serum albumin). The cultivation was continued for further 6 days with replacing the medium at intervals of 3 days.

After removing the medium, an Opti-MEM medium (containing 5 mg/ml of bovine serum albumin) containing 5 ug (microgram)/ml of the above rosemary extract was added to each well in an amount of 50 ul (microliter) /well, and the cultivation was continued for further 4 days. After the cultivation, the supernatant was taken as a sample solution.

On the other hand, 1 ug/ml of an anti-NGF antibody (Promega) solution (50 ul) was added to each well of a 96-well microplate (Nunc), and the plate was allowed to stand overnight at 4° C. After washing the plate with PBS(−) (Nissui Pharmaceuticals), 1% of a bovine serum albumin (Sigma) solution (100 ul) was added to each well of the plate and the plate was allowed to stand at room temperature for 4 hrs. Subsequently, the plate was washed with PBS (−) and the above sample solution (50 ul) was added to each well of the plate. After the reaction at room temperature for one hour, the plate was washed with PBS (−).

Subsequently, 0.4 unit/ml of an beta-galactosidase-labeled anti-NGF antibody (Boehringer Mannheim) solution (50 ul) was added to each well of the plate, and allowed to react at room temperature for one hour. After washing the plate with PBS (−), 0.5 mg/ml of a 4-methylumbelliferyl-beta-D-galactoside solution (200 ul) was added to each well of the plate, and allowed to react overnight at room temperature. The fluorescence intensity of 4-methylumbelliferone produced was measured on a fluorescence plate reader, and the content of NGF contained in the sample solution was determined using a standard curve obtained from a standard solution (human beta-NGF; PEPRO TECH EC). The results are shown in Table 1 below.

Example 2

The content of NGF contained in the sample solution was determined as described in Example 1, except that an Opti-MEM medium (containing 5 mg/ml of bovine serum albumin) containing 10 ug/ml of the rosemary extract of Example 1 was used in an amount of 50 ul/well, instead of the Opti-MEM medium containing 5 ug/ml of the rosemary extract. The results are shown in Table 1 below.

Comparative Example 1

The content of NGF contained in the sample solution was determined as described in Example 1, except that an Opti-MEM medium (containing 5 mg/ml of bovine serum albumin) not containing the rosemary extract of Example 1 was used in an amount of 50 ul/well, instead of the Opti-MEM medium containing 5 ug/ml of the rosemary extract. The results are shown in Table 1 below.

TABLE 1

| | Effective ingredient | Concentration (ug/ml)*1 | NGF Content in sample solution (pg/ml)*2 | Relative NGF content*3 |
|---|---|---|---|---|
| Example 1 | Rosemary extract | 5 | 12.9 ± 1.7 | 2.1 |
| Example 2 | Rosemary extract | 10 | 15.6 ± 3.3 | 2.5 |
| Comparative example 1 | none | 0 | 6.2 ± 0.5 | 1.0 |

*1Concentration of effective ingredient in medium
*2NGF Content shown by mean measurements ± standard deviation
*3Ratio of example solutions to comparative example solution Example 3

Sage (whole plant, 60 g) was soaked in ethanol (300 ml), and the mixture was allowed to stand overnight at room temperature. The resultant solution was then concentrated to a volume of 100 ml. The concentrated solution was filtered to remove insoluble materials. Purified water (600 ml) was added to the filtrate and the mixture was allowed to stand overnight at 4° C. Subsequently, the mixture was again filtered to obtain a sage extract (dry weight 4 g) which is insoluble part. The content of NGF contained in the sample solution was determined as described in Example 1, except that the sage extract was used instead of the rosemary extract. The results are shown in Table 2 below.

Example 4

The content of NGF contained in the sample solution was determined as described in Example 1, except that an Opti-MEM medium (containing 5 mg/ml of bovine serum albumin) containing 10 ug/ml of the sage extract of Example 3 was used in an amount of 50 ul/well, instead of the Opti-MEM medium containing 5 ug/ml of the rosemary extract. The results are shown in Table 2 below.

Comparative Example 2

The content of NGF contained in the sample solution was determined as described in Example 1, except that an Opti-MEM medium (containing 5 mg/ml of bovine serum albumin) not containing the sage extract of Example 3 was used in an amount of 50 ul/well, instead of the Opti-MEM medium containing 5 ug/ml of the rosemary extract. The results are shown in Table 2 below.

TABLE 2

|  | Effective ingredient | Concentration (ug/ml)*1 | NGF Content in sample solution (pg/ml)*2 | Relative NGF content*3 |
|---|---|---|---|---|
| Example 3 | Sage extract | 5 | 17.4 ± 1.6 | 2.6 |
| Example 4 | Sage extract | 10 | 28.4 ± 1.6 | 4.2 |
| Comparative example 2 | none | 0 | 6.8 ± 0.3 | 1.0 |

*1Concentration of effective ingredient in medium
*2NGF Content shown by mean measurements ± standard deviation
*3Ratio of example solutions to comparative example solution As shown in Tables 1 and 2, it is evident that the content of NGF in the sample solution increases in the systems containing the rosemary or sage extract according to the present invention (Examples 1 to 4), as compared with the systems not containing any effective ingredient (Comparative Examples 1 and 2). It is also evident that the higher the concentration of the effective ingredient used, the more the amount of NGF produced.

Example 5

Rosemary (whole plant, 5 kg) was soaked in ethanol (20 L), and extracted at 40° C. for 72 hrs. The resultant solution was concentrated to a volume of 1 L. After the concentration, the concentrate was filtered to remove insoluble materials. Purified water (2 L) was added to the filtrate and the precipitate (105 g) deposited at this time was filtered. The precipitate was dissolved in ethyl acetate, and separated and purified through a silica gel column chromatography (developing solvent; ethyl acetate:hexane=1:4 (v/v)). The crystals obtained by removing the solvent were recrystallized in hexane to obtain pale yellow crystal 1 (1.5 g) and white crystal 2 (0.8 g). $^{13}$C-NMR and $^1$H-NMR spectra (CDCl$_3$) of crystals 1 and 2 are shown in the following Tables 3 and 4, respectively.

TABLE 3

NMR spectra of crystal 1

| $^{13}$C, δ(ppm) | $^1$H, δ(ppm) |
|---|---|
| 34.4(t); 20.3(t); | 1.24(1H,m) and 3.29(1H,m); |
| 41.8(t); 34.4(s); | 1.60(1H,m) and 1.75(1H,m); |
| 54.0(d); 18.9(t); | 1.32(1H,m) and 1.50(1H,dt); |
| 31.5(t); 129.0(s); | 1.57(1H,dd); |
| 122.1(s); 48.7(s); | 1.86(1H,m) and 2.36(1H,m); |
| 142.1(s); 141.4(s); | 2.85(2H,m); 6.64(1H,s); |
| 133.8(s); 119.4(d); | 3.17(1H,m); 1.21(3H,d); |
| 27.2(d); 22.1(q); | 1.20(3H,d); 0.89(3H,s); |
| 22.5(q); 32.6(q); | 1.00(3H,s); 6.56(2H,s); |
| 21.7(q); 183.1(s) | 7.36(1H,s) |

TABLE 4

NMR spectra of crystal 2

| $^{13}$C, δ(ppm) | $^1$H, δ(ppm) |
|---|---|
| 30.0(t); 19.9(t); | 2.81(1H,m) and 2.51(1H,td); |
| 42.2(t); 35.2(s); | 1.97(1H,m) and 1.533(1H,m); |
| 46.5(d); 30.8(t); | 1.27(1H,m) and 1.474(1H,m); |
| 78.1(d); 123.7(s); | 1.64(1H,dd); |
| 133.2(s); 49.2(s); | 1.77(1H,m) and 2.144(1H,m); |
| 144.0(s); 144.1(s); | 5.28(2H,dd); 6.64(1H,s); |
| 134.7(s); 112.1(d); | 3.22(1H,m); 1.18(3H,d); |
| 27.2(d); 23.0(q); | 1.17(3H,d); 0.87(3H,s); |
| 23.1(q); 20.1(q); | 0.83(3H,d); |
| 32.2(q); 175.2(s) | 7.7–7.2(2H,OH) |

From the results of NMR spectra, it was found that crystal 1 is carnosic acid of the above formula (I) and crystal 2 is carnosol of the above formula (II).

Carnosic acid of the formula (I) obtained as described above was used as an effective ingredient. The content of NGF contained in the sample solution was determined as described in Example 1, except that an Opti-MEM medium (containing 5 mg/ml of bovine serum albumin) containing carnosic acid of the formula (I) at a concentration of 20 uM was used in an amount of 50 ul/well, instead of the Opti-MEM medium containing 5 ug/ml of the rosemary extract. The results are shown in Table 5 below.

Example 6

The content of NGF contained in the sample solution was determined as described in Example 1, except that an Opti-MEM medium (containing 5 mg/ml of bovine serum albumin) containing carnosic acid of the formula (I) at a concentration of 100 uM was used in an amount of 50 ul/well, instead of the Opti-MEM medium containing 5 ug/ml of the rosemary extract. The results are shown in Table 5 below.

Example 7

Carnosol of the formula (II) obtained in Example 5 was used as an effective ingredient. The content of NGF contained in the sample solution was determined as described in Example 1, except that an Opti-MEM medium (containing 5 mg/ml of bovine serum albumin) containing carnosol of the formula (II) at a concentration of 20 uM was used in an amount of 50 ul/well, instead of the Opti-MEM medium containing 5 ug/ml of the rosemary extract. The results are shown in Table 5 below.

Example 8

The content of NGF contained in the sample solution was determined as described in Example 1, except that an Opti-MEM medium (containing 5 mg/ml of bovine serum albumin) containing carnosol of the formula (II) at a concentration of 100 uM was used in an amount of 50 ul/well, instead of the Opti-MEM medium containing 5 ug/ml of the rosemary extract. The results are shown in Table 5 below.

Comparative Example 3

The content of NGF contained in the sample solution was determined as described in Example 1, except that an Opti-MEM medium (containing 5 mg/ml of bovine serum albumin) not containing any effective ingredient was used in an amount of 50 ul/well, instead of the Opti-MEM medium containing 5 ug/ml of the rosemary extract. The results are shown in Table 5 below.

TABLE 5

| | Effective ingredient | Concentration (uM)*1 | NGF Content in sample solution (pg/ml)*2 | Relative NGF content*3 |
|---|---|---|---|---|
| Example 5 | Carnosic acid of formula (I) | 20 | 46.0 ± 7.4 | 7.2 |
| Example 6 | Carnosic acid of formula (I) | 100 | 158.5 ± 16.6 | 24.8 |
| Example 7 | Carnosol of formula (II) | 20 | 35.4 ± 6.9 | 5.5 |
| Example 8 | Carnosol of formula (II) | 100 | 39.9 ± 2.3 | 6.2 |
| Comparative example 3 | none | 0 | 6.4 ± 0.3 | 1.0 |

*1Concentration of effective ingredient in medium
*2NGF Content shown by mean measurements ± standard deviation
*3Ratio of example solutions to comparative example solution As shown in Table 5, it is evident that the content of NGF in the sample solution increases in the systems containing carnosic acid of the formula (I) (Examples 5 and 6) or carnosol of the formula (II) (Examples 7 and 8) according to the present invention, as compared with the system not containing any effective ingredient (Comparative Example 3). It is also evident that the higher the concentration of the effective ingredient used, the more the amount of NGF produced.

According to the present method, it is possible to efficiently promote the synthesis of NGF. The present method safely promotes production of NGF in the living body without accompanying side effects, such as loss of a quantitative balance of hormones in the living body. It is expected by the increase of NGF in the living body that nerve-denaturing diseases, such as Alzheimer-type dementia and brain ischemia pathologies, are prevented and treated.

What is claimed is:

1. A method of promoting the synthesis of nerve growth factor comprising administering to a subject requiring such promotion an effective amount of at least one plant extract, which has an effect of promoting the synthesis of nerve growth factor, wherein the plant extract is a member selected from the group consisting of rosemary extract, sage extract and a mixture thereof.

2. The method according to claim 1 wherein the rosemary extract and the sage extract are obtained by extracting each of rosemary and sage separately with ethanol or with a mixture of water and ethanol.

3. The method according to claim 1 wherein the plant extract is administered in the form of a drug or food composition.

4. A method of promoting the synthesis of nerve growth factor comprising administering an effective amount of at least one ingredient selected from the group consisting of carnosic acid, carnosol and a mixture thereof to a subject requiring such promotion.

5. The method according to claim 4 wherein the ingredient is administered in the form of a drug or food composition.

6. The method according to claim 2, wherein the plant extract is administered in the form of a drug or food composition.

7. A method according to claim 4 wherein the carnosic acid is a compound of formula I,

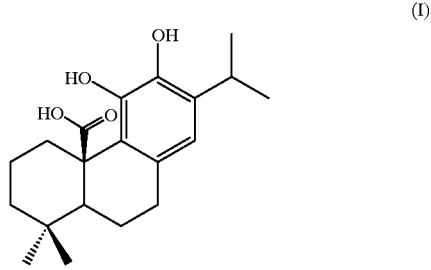

(I)

and the carnosol is a compound of formula II

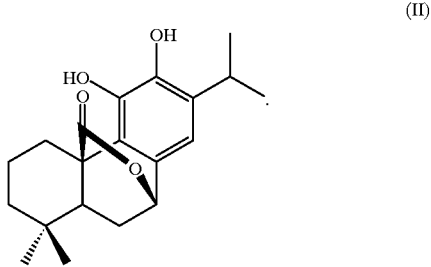

(II)

* * * * *